US012691396B2

(12) United States Patent
Kusters et al.

(10) Patent No.: US 12,691,396 B2
(45) Date of Patent: Jul. 28, 2026

(54) FLUID PROCESSING CASSETTE WITH INTEGRATED FILTER

(71) Applicant: Fenwal, Inc., Lake Zurich, IL (US)

(72) Inventors: Benjamin E. Kusters, Pleasant Prairie, WI (US); Mark J. Brierton, Cary, IL (US)

(73) Assignee: Fenwal, Inc., Lake Zurich, IL (US)

( * ) Notice: Subject to any disclaimer, the term of this patent is extended or adjusted under 35 U.S.C. 154(b) by 476 days.

(21) Appl. No.: 18/120,563

(22) Filed: Mar. 13, 2023

(65) Prior Publication Data

US 2023/0285880 A1     Sep. 14, 2023

Related U.S. Application Data

(60) Provisional application No. 63/319,603, filed on Mar. 14, 2022.

(51) Int. Cl.
*B01D 35/30*     (2006.01)
*A61M 1/02*     (2006.01)
*B01D 29/03*     (2006.01)

(52) U.S. Cl.
CPC .......... *B01D 35/30* (2013.01); *A61M 1/0272* (2013.01); *B01D 29/03* (2013.01);
(Continued)

(58) Field of Classification Search
CPC .. B01D 35/30; B01D 29/03; B01D 2201/182; B01D 2201/303; A61M 1/0272;
(Continued)

(56) References Cited

U.S. PATENT DOCUMENTS 4,701,267 A * 10/1987 Watanabe .......... B01D 39/1623
                                                      210/806
2004/0127841 A1* 7/2004 Briggs ................ A61M 1/3681
                                                      210/781
(Continued)

FOREIGN PATENT DOCUMENTS

EP          3287153 A1      2/2018
WO      2017085372 A1      5/2017
WO      2018046842 A1      3/2018

OTHER PUBLICATIONS

European Search Report and Written Opinion issued Jun. 29, 2023, for European Application No. 23161387.8.

*Primary Examiner* — Madeline Gonzalez
(74) *Attorney, Agent, or Firm* — Cook Alex Ltd.

(57)                    ABSTRACT

Biological fluid processing cassettes with integrated filter structures are disclosed. A cassette body is formed of a generally rigid material, defining a plurality of internal fluid flow paths. The cassette body may be secured to a cassette cap to define a cavity, with a filter sealed within the cavity. Each of the cassette body and the cassette cap defines a port opening into the cavity, which allows fluid to flow from one of the internal fluid flow paths, into the cavity and through the filter, and then out of the cavity via the port of the cassette cap. Alternatively, the cassette body may define an external slot which receives at least a portion of a filter. Such a filter includes two ports, with one of the ports in fluid communication with a cassette port of the cassette body to allow fluid flow between the cassette body and the filter.

21 Claims, 13 Drawing Sheets

(52) U.S. Cl.
CPC ............... *A61M 2202/0439* (2013.01); *B01D 2201/182* (2013.01); *B01D 2201/303* (2013.01)

(58) Field of Classification Search
CPC .... A61M 2202/0439; A61M 2205/125; A61M 1/3635; A61M 1/36226
USPC ....... 210/435, 439, 455, 782, 767, 645, 446, 210/451, 456
See application file for complete search history.

(56) References Cited

U.S. PATENT DOCUMENTS

2010/0282681 A1*  11/2010  Zuk, Jr. ............... A61M 1/0218
                                                        210/651
2011/0151463 A1*   6/2011  Wulfman .............. A61M 27/00
                                                        435/6.12

* cited by examiner

FLUID PROCESSING CASSETTE WITH INTEGRATED FILTER

CROSS-REFERENCE TO RELATED APPLICATIONS

This application claims the benefit of and priority of U.S. Provisional Patent Application Ser. No. 63/319,603, filed Mar. 14, 2022, the contents of which are incorporated by reference herein.

BACKGROUND

Field of the Disclosure

The present disclosure generally relates to filters used in the collection and processing of blood and blood components or other biological fluids. More particularly, the present disclosure relates to filters integrated with a fluid processing cassette.

Description of Related Art

Using various manual and automated systems and methods, whole blood is collected and separated into its clinical components (typically red blood cells, platelets, and plasma). The collected components are typically individually stored and used to treat a variety of specific conditions and diseased states.

Before transfusing the collected blood components to a recipient in need of the components, or before subjecting blood components to treatment (such as, but not limited to, pathogen inactivation), it is often desirable to minimize the presence of impurities or other materials that may cause undesired side effects in the recipient. For example, because of possible reactions, it is generally considered desirable to reduce the number of leukocytes in blood components before storage, or at least before transfusion (i.e., "leukoreduction").

Filters are widely used to accomplish leukoreduction in blood products today (e.g., warm and cold filtration of leukocytes from whole blood, red cells, and/or platelet products). Filters typically include a filter media disposed between mating walls of a filter housing. Inlet and outlet ports associated with the housing provide flow paths to and from the interior of the filter. The walls of the housing may be made of a rigid, typically plastic, material, although filters including soft housings are also known. Due to the importance of filtering blood or blood components, there exists an ongoing desire to improve the construction, performance, and manufacturability of biological fluid filters.

Typically, a filter is a separate piece of equipment installed on an automated system housing. Although this provides adequate functionality, it adds additional space to the footprint of the device and additional complexity to the process. Thus, it would be advantageous to include a filter in an existing portion of the automated system in order to decrease device footprint and complexity of installation.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a biological fluid processing cassette includes a rigid cassette body defining a cavity and an inlet port opening into the cavity, a rigid cap secured to the cassette body to seal the cavity and defining an outlet port opening into the cavity, and a filtration medium sealed within the cavity for filtration of a biological fluid flowing through the cavity from the inlet port to the outlet port.

In another aspect, a biological fluid processing cassette includes a rigid cassette body with a slot configured to receive a filter and a filter within the slot of the cassette body, the filter including an inlet port and an outlet port. The body includes at least one outlet port for flowing fluid from the cassette to the filter.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

The current disclosure includes biological fluid processing cassettes and may be utilized in blood processing systems, although they can be more widely used. As will be described in greater detail herein, biological fluid processing cassettes according to the present disclosure incorporate a filter into the design of the cassette, alleviating the need for a hardware component to include a dedicated receptacle for the filter.

Figure 1:
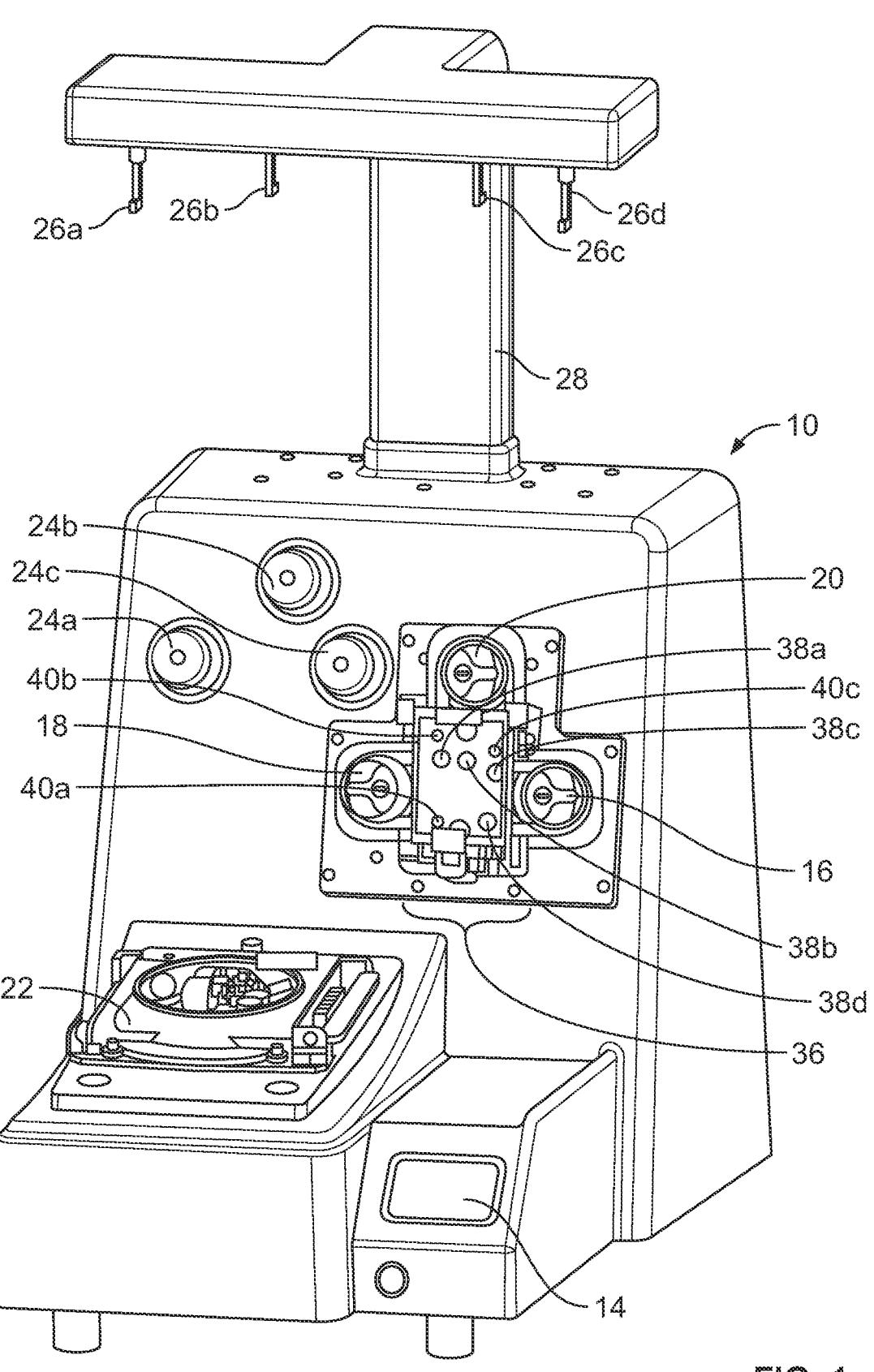
FIG. 1 is a perspective view of an exemplary reusable hardware component of a biological fluid processing system which is configured to receive a disposable fluid flow circuit.
Figure 2:
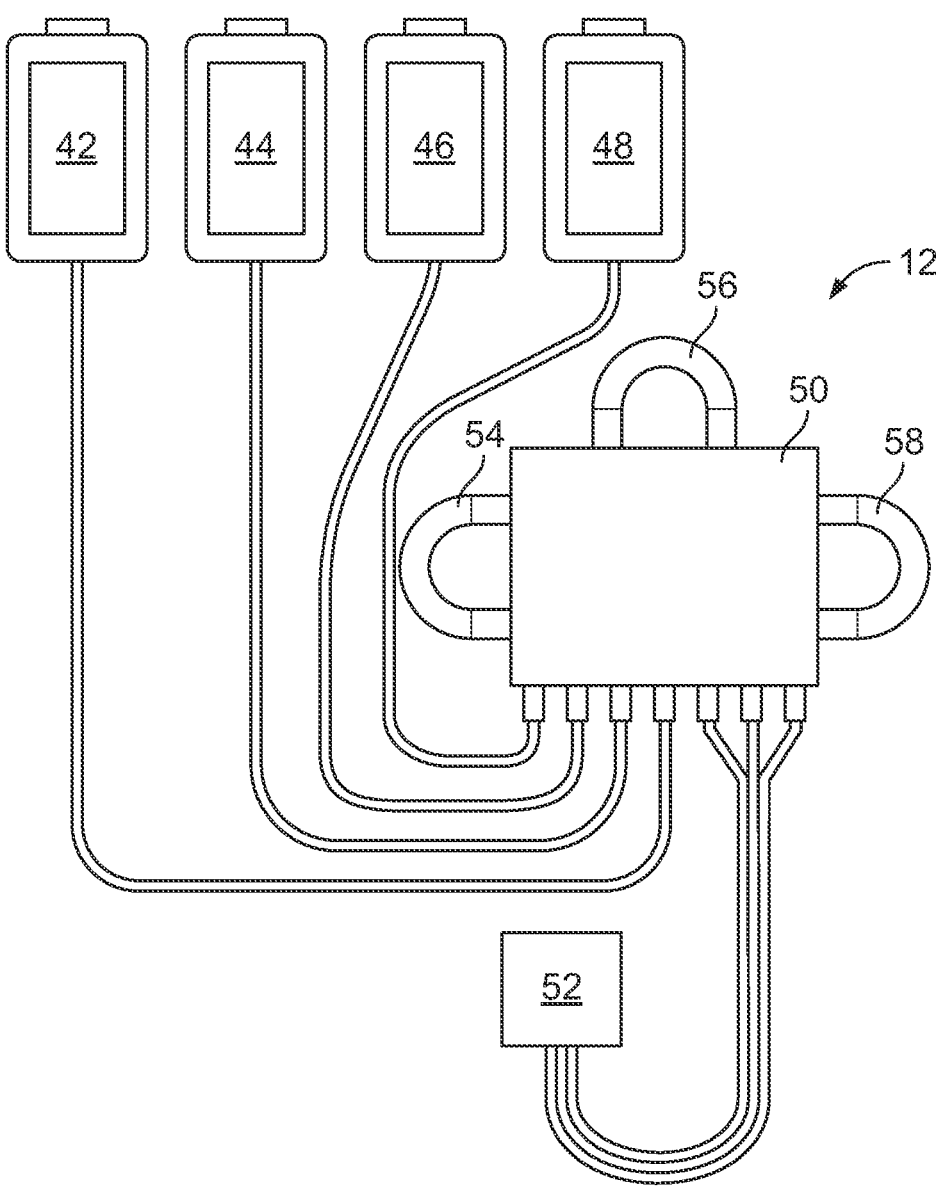
FIG. 2 is a schematic view of a disposable flow set suitable for use with the processing device shown in FIG. 1.

FIG. 1 depicts one example of a reusable hardware component or processing device 10 of a biological fluid processing system that can be used with the biological fluid processing cassettes described in the exemplary embodiments of the current disclosure. FIG. 2 depicts a disposable fluid flow circuit, generally designated 12, that is suitable to be used in combination with the processing device 10 for processing collected whole blood or another biological fluid. The illustrated processing device 10 includes associated pumps, valves, sensors, displays, and other components for configuring and controlling flow of fluid through the fluid flow circuit 12, described in greater detail below. It should be understood that the processing device 10 of FIG. 1 and the fluid flow circuit 12 of FIG. 2 are merely exemplary and that the present disclosure encompasses differently configured processing devices and fluid flow circuits.

More specifically, the illustrated processing device 10 includes a user input and output touchscreen 14, a pump station including a first pump 16 (for pumping, e.g., whole blood), a second pump 18 (for pumping, e.g., plasma) and a third pump 20 (for pumping, e.g., additive solution), a centrifuge mounting station and drive unit 22 (which may be referred to herein as a "centrifuge"), and clamps 24a-c. The touchscreen 14 enables user interaction with a controller of the processing device 10 (which may be pre-programmed to automatically operate the system to perform one or more standard biological fluid processing procedures selected by an operator), as well as the monitoring of procedure parameters, such as flow rates, container weights, pressures, etc. The pumps 16, 18, and 20 (collectively referred to herein as being part of a "pump system" of the processing device 10) are illustrated as peristaltic pumps capable of receiving tubing or conduits and moving fluid at various rates through the associated conduit dependent upon the procedure being performed. An exemplary centrifuge mounting station/drive unit is seen in U.S. Pat. No. 8,075,468 (with reference to FIGS. 26-28), which is hereby incorporated herein by reference. The clamps 24a-c (collectively referred to herein as being part of the "valve system" of the processing device 10) are capable of opening and closing fluid paths through the tubing or conduits and may incorporate RF sealers in order to complete a heat seal of the tubing or conduit placed in the clamp to seal the tubing or conduit leading to a product container upon completion of a procedure.

The processing device 10 also includes hangers 26a-d (which may each be associated with a weight scale) for suspending the various containers of the disposable fluid circuit 12. The hangers 26a-d are preferably mounted to a support 28, which is vertically translatable to improve the transportability of the processing device 10.

The face of the processing device 10 includes a nesting module 36 for seating a flow control cassette 50 (FIG. 2) of the fluid flow circuit 12. The cassette nesting module 36 is configured to receive various disposable cassette designs so that the system may be used to perform different types of procedures. Embedded within the illustrated cassette nesting module 36 are four valves 38a-d (collectively referred to herein as being part of the "valve system" of the processing device 10) for opening and closing fluid flow paths within the flow control cassette 50, and three pressure sensors 40a-c capable of measuring the pressure at various locations of the flow control cassette 50.

With reference to FIG. 2, the illustrated fluid flow circuit 12 includes a plurality of containers 42, 44, 46, and 48 with a flow control cassette 50 and a processing/separation chamber 52 that is configured to be received in the centrifuge 22, all of which are interconnected by conduits or tubing segments, so as to permit continuous flow centrifugation. The flow control cassette 50 routes the fluid flow through three tubing loops 54, 56, 58, with each loop being positioned to engage a particular one of the pumps 16, 18, 20. The conduits or tubing may extend through the cassette 50, or the cassette 50 may have pre-formed internal fluid flow paths that direct the fluid flow (such as L1-L13 of FIG. 3).

The containers 42, 44, 46, and 48 may be configured to hold a variety of different biological and non-biological fluids, depending on the nature of the procedure to be executed. The fluid flow circuit 12 may also be provided with a different number of containers without departing from the scope of the present disclosure. In one exemplary embodiment, container 42 of the fluid flow circuit 12 shown in FIG. 2 may be pre-filled with additive solution, container 44 may be filled with whole blood and connected to the fluid flow circuit 12 at the time of use, container 46 may be an empty container for the receipt of red blood cells separated from the whole blood, and container 48 may be an empty container for the receipt of plasma separated from the whole blood. While FIG. 2 shows a whole blood container 44 (configured as a blood pack unit, for example) as a blood source, it is within the scope of the present disclosure for the blood source to be a living donor.

Figure 3:
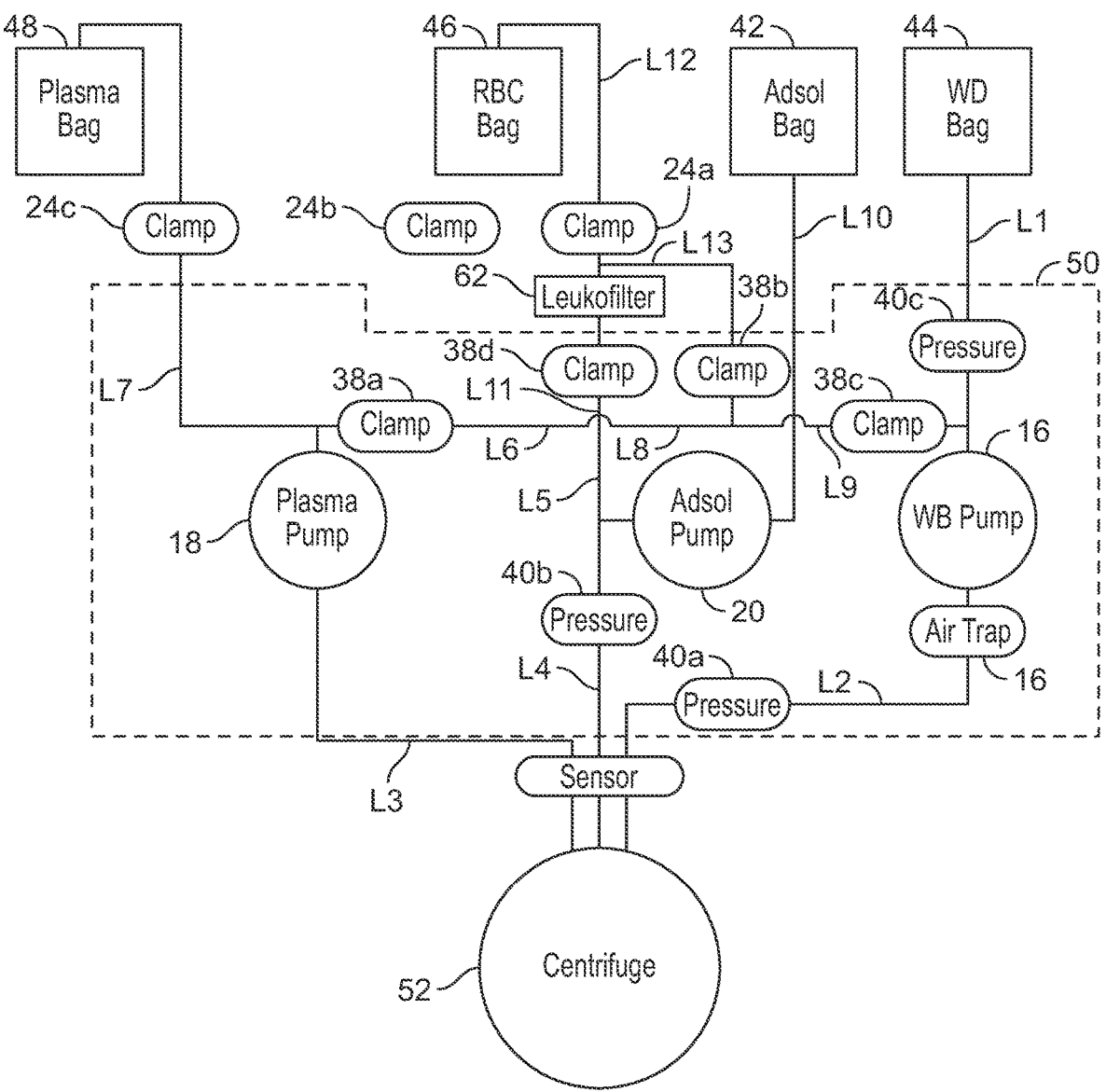
FIG. 3 is a schematic view of a biological fluid processing circuit defined by a cassette of the flow set of FIG. 2, which can be programmed to perform a variety of different biological fluid processing procedures in association with the device shown in FIG. 1.

The fluid flow circuit 12 may include a variety of other features and components without departing from the scope of the present disclosure. For example, FIG. 3 illustrates a flow control cassette 50 (represented in FIG. 3 by a dashed line) including an air trap 60 (through which a fluid to be processed is flowed prior to entering the separation chamber 52). FIG. 3 shows a leukoreduction filter 62 (through which the red blood cells are flowed prior to entering the red blood cell collection container 46) positioned externally of the cassette 50, which represents a conventional configuration in which the device 10 requires a dedicated receptacle for the filter 62. Possible configurations in which a filter (including, but not limited to a leukoreduction filter 62) is incorporated into the flow control cassette 50 will be described in greater detail herein. While FIG. 3 illustrates pumps, clamps, and sensors within the flow control cassette 50, it should be understood that such components are incorporated into the processing device 10 (as described above), with the flow control cassette 50 defining formations configured to interact with the components of the processing device 10 (e.g., tubing loops configured to associate with the pumps, valve chambers configured to associate with the clamps, and sensing chambers configured to associate with the sensors).

The various components of the set 12 are connected by flexible tubing to ports of the flow control cassette 50. The cassette 50 provides a centralized, programmable, integrated platform for all the pumping and valving functions required for a given biological fluid processing procedure. In use, the cassette 50 is mounted to the cassette nesting module 36 of the device 10. The clamps of the module 36 apply positive and negative pneumatic pressure to associated valve chambers of the cassette 50 to control and direct liquid flow therethrough, while the pumps act upon tubing loops extending from the cassette 50 to convey fluid into and out of the cassette 50. The operation of the pumps and valves to control fluid flow through the cassette 50 can be understood with reference to U.S. Patent Application Publication No. 2009/0215602, which is hereby incorporated herein by reference.

It is again emphasized that the illustrated processing device 10 and associated fluid flow circuit 12 are merely exemplary and may be differently configured (e.g., using pneumatic pumps instead of peristaltic pumps and/or a spinning membrane separator instead of a centrifugal separation chamber) without departing from the scope of the present disclosure. Most notably, the cassette 50 of the fluid flow circuit 12 and the associated filter 62 may be variously configured, such as with a filter configured to receive a biological fluid to be processed, rather than one configured to receive a separated fluid component (as shown in FIG. 3). A first exemplary biological fluid processing cassette 150 is shown in FIGS. 4-8 and a second exemplary biological fluid processing cassette 250 is shown in FIGS. 9-13.

Figure 5:
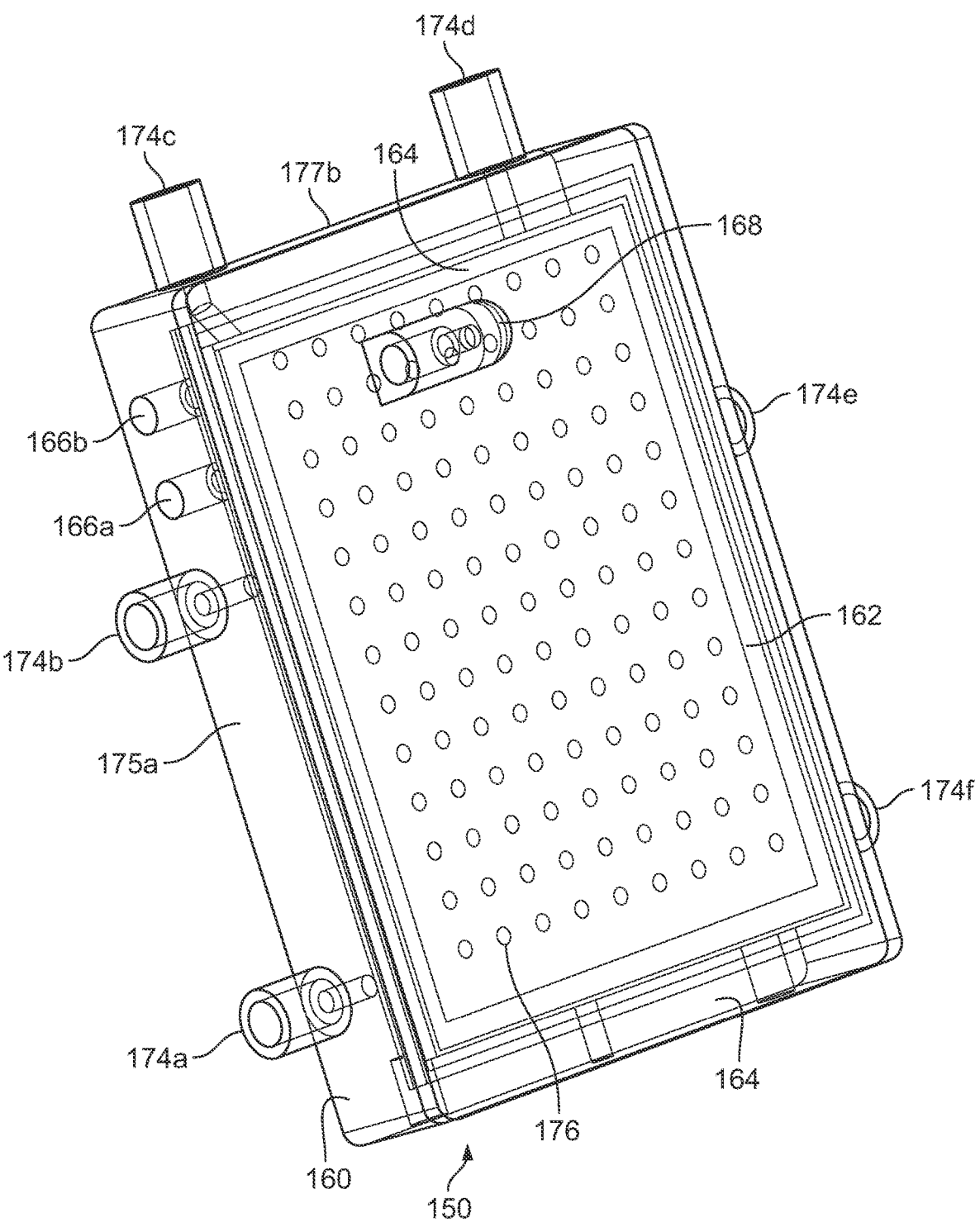
FIG. 5 is a perspective transparent view of the first fluid processing cassette of FIG. 4.
Figure 6:
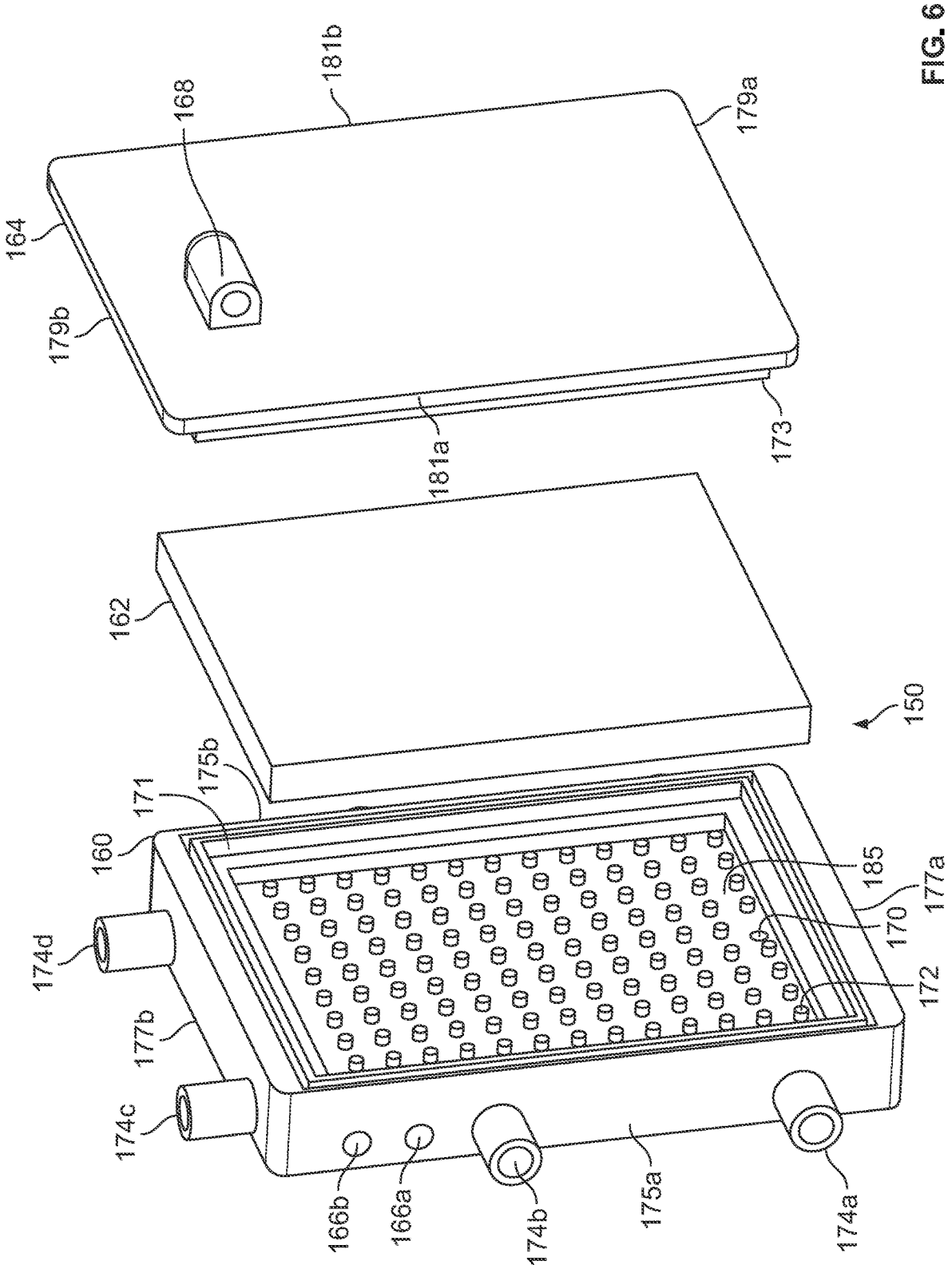
FIG. 6 is a perspective exploded view of the first fluid processing cassette of FIG. 4.
Figure 7:
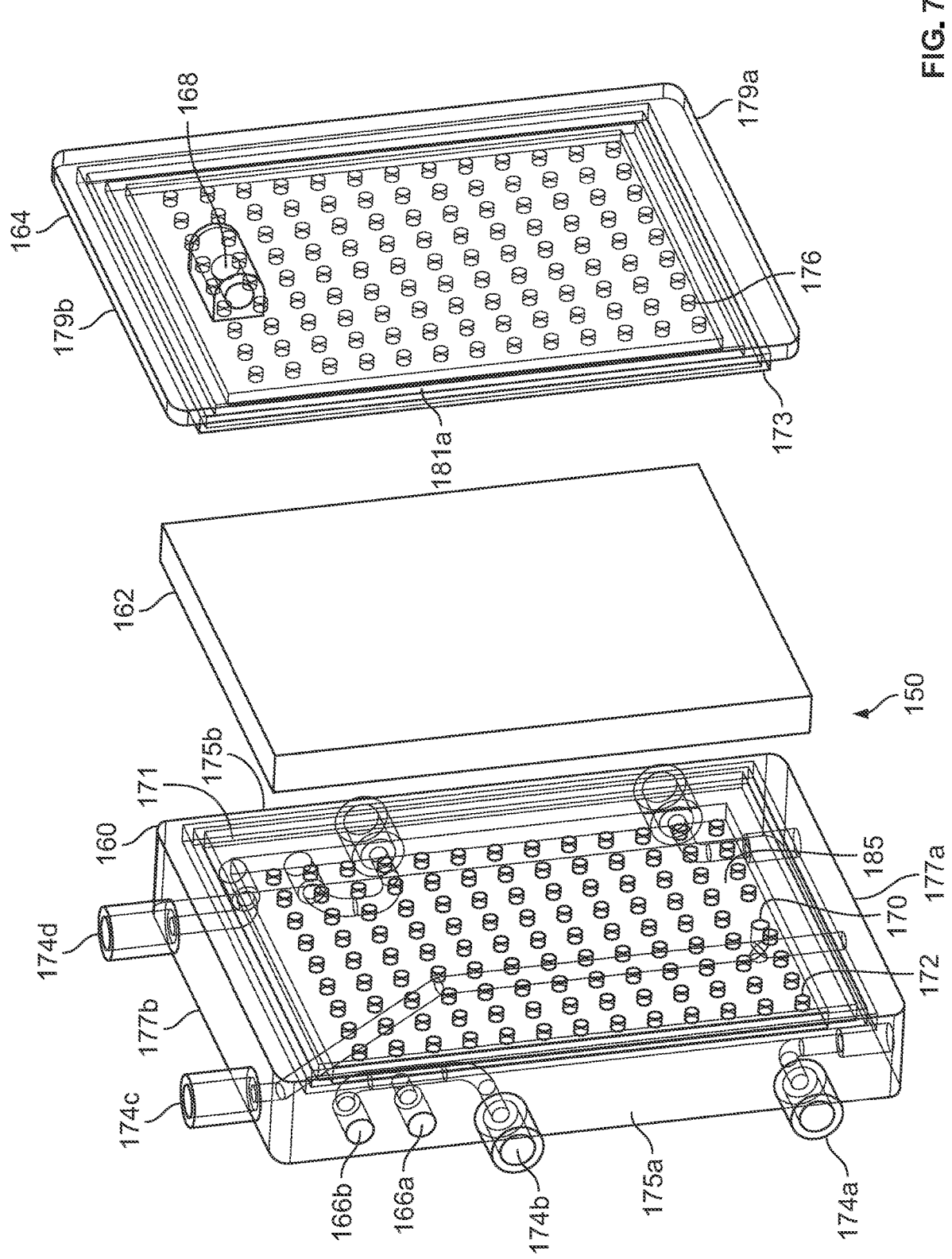
FIG. 7 is a transparent perspective exploded view of the first fluid processing cassette of FIG. 4.

In the embodiment of FIGS. 4-8, the cassette 150 includes a cassette body 160 having a perimeter defined by first and second sides or edges 175a and 175b and bottom and top sides or edges 177a and 177b. As can be more clearly seen in FIGS. 6 and 7, the cassette body includes a first wall or face 185 extending between the edges, with a opposite second wall or face (not visible) spaced from the first wall or face 185. As best shown in FIG. 7, a plurality of internal fluid flow paths are defined by the cassette body 160, with the internal fluid flow paths defining the manner in which fluid is directed through the cassette 150. When it is stated that the fluid flow paths are "defined" by the cassette body 160, it should be understood that this encompasses fluid flow paths molded into the rigid body 160 and fluid flow paths that are simply positioned within the body 160 (e.g., flexible or rigid tubes or conduits). In addition to the various fluid flow paths, the body 160 may define other features of the cassette 150, such as valve and sensor chambers.

The cassette 150 also includes a cassette cap 164 with first and second sides or edges 181a and 181b and bottom and tops sides or edges 179a and 179b. The cassette cap 164 is configured to be secured to the body 160 (as will be described in greater detail), with the cap 164 positioned generally adjacent to the first wall or face 185 of the body 160. In view of this, it may be advantageous for the edges of the cassette cap 164 to be configured to define a perimeter that matches the perimeter of the body 160, such that the perimeter of the cassette 150 has a generally smooth or continuous perimeter when the cap 164 is secured to the body 160.

Preferably, the body 160 and cap 164 are comprised of rigid materials, such as a medical grade plastic material. As the body 160 and cap 164 are configured to be secured to each other, it may be advantageous for them to be formed of the same material (in order to facilitate the two components being secured together), though it is within the scope of the present disclosure for the body 160 and cap 164 to be formed of different materials. Suitable materials include (without limitation) any biocompatible plastic, including acrylic and acrylonitrile butadiene styrene (ABS).

The body 160 and cap 164 include or define a number of ports or openings in which fluid may flow into or out of the cassette 150. The ports may be molded into the cassette 150 or may secured to the associated surfaces of the cassette body or cap by any suitable means (e.g., being heat sealed thereto using radio-frequency energy). Those having skill in the art will appreciate that each port of the cassette 150 may be associated with a variety of components and tasks, such as being in fluid communication with the separation chamber, a red blood cell collection container, a plasma collection container, a platelet collection container, an anticoagulant container, a platelet storage solution container, a red blood cell additive solution container, a saline container, etc. The ports can be connected to each of these containers/devices by flexible tubing or any other suitable conduit.

In the illustrated embodiment, the perimeter of the body 160 includes ports 166a and 166b, configured to be connected to the tubing of a fluid flow circuit 12. One of the ports may be configured to provide an inlet through which biological fluid may enter the cassette 150, with the other providing an outlet for a separated fluid component or a processed fluid. It should be understood that the body 160 may include a plurality of other ports (as in FIGS. 2 and 3) to allow the cassette 150 to communicate with additional components of the fluid flow circuit 12.

Figure 8:
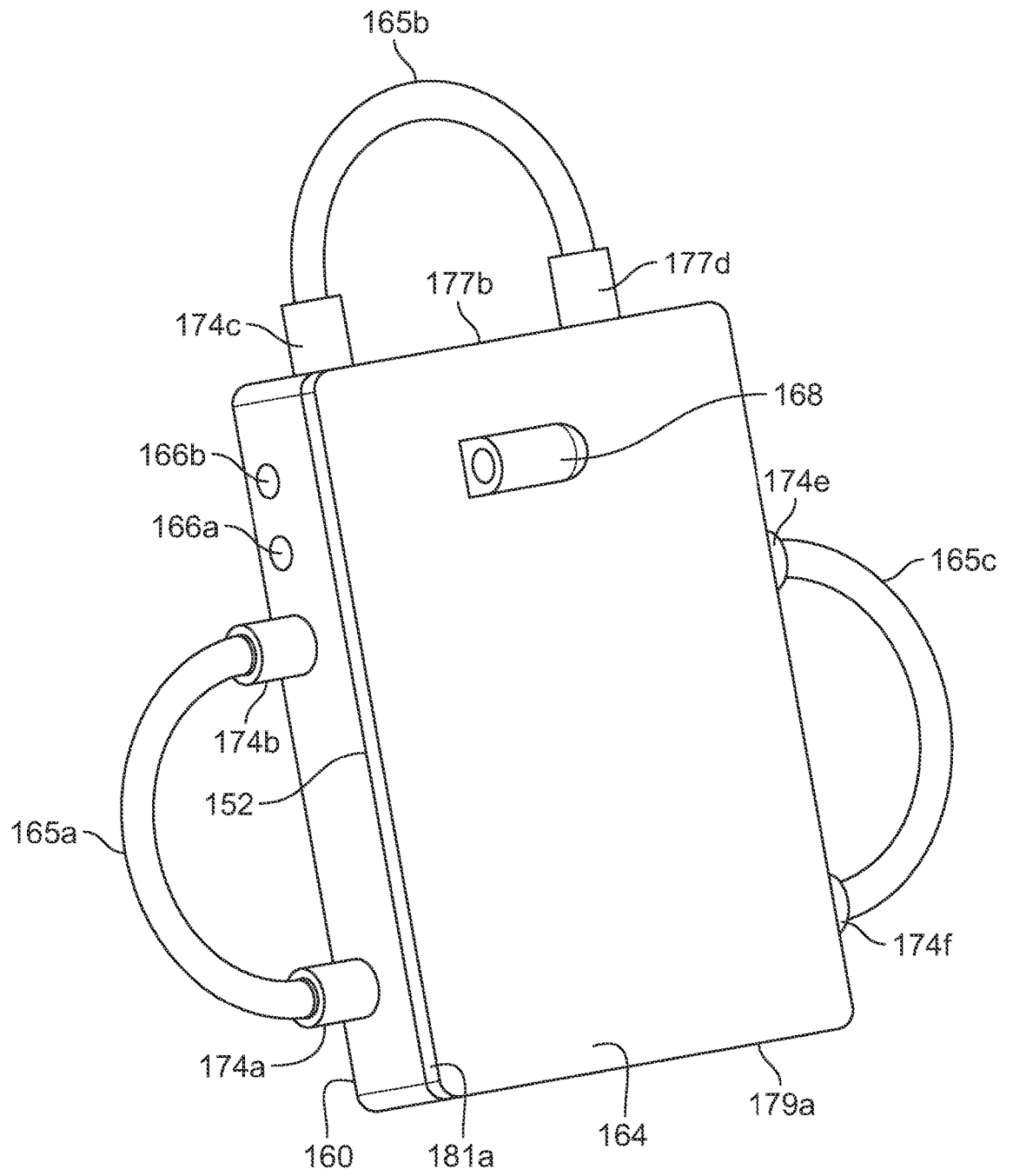
FIG. 8 is a perspective view of the first fluid processing device of FIG. 4 with pump tubing included.
Figure 9:
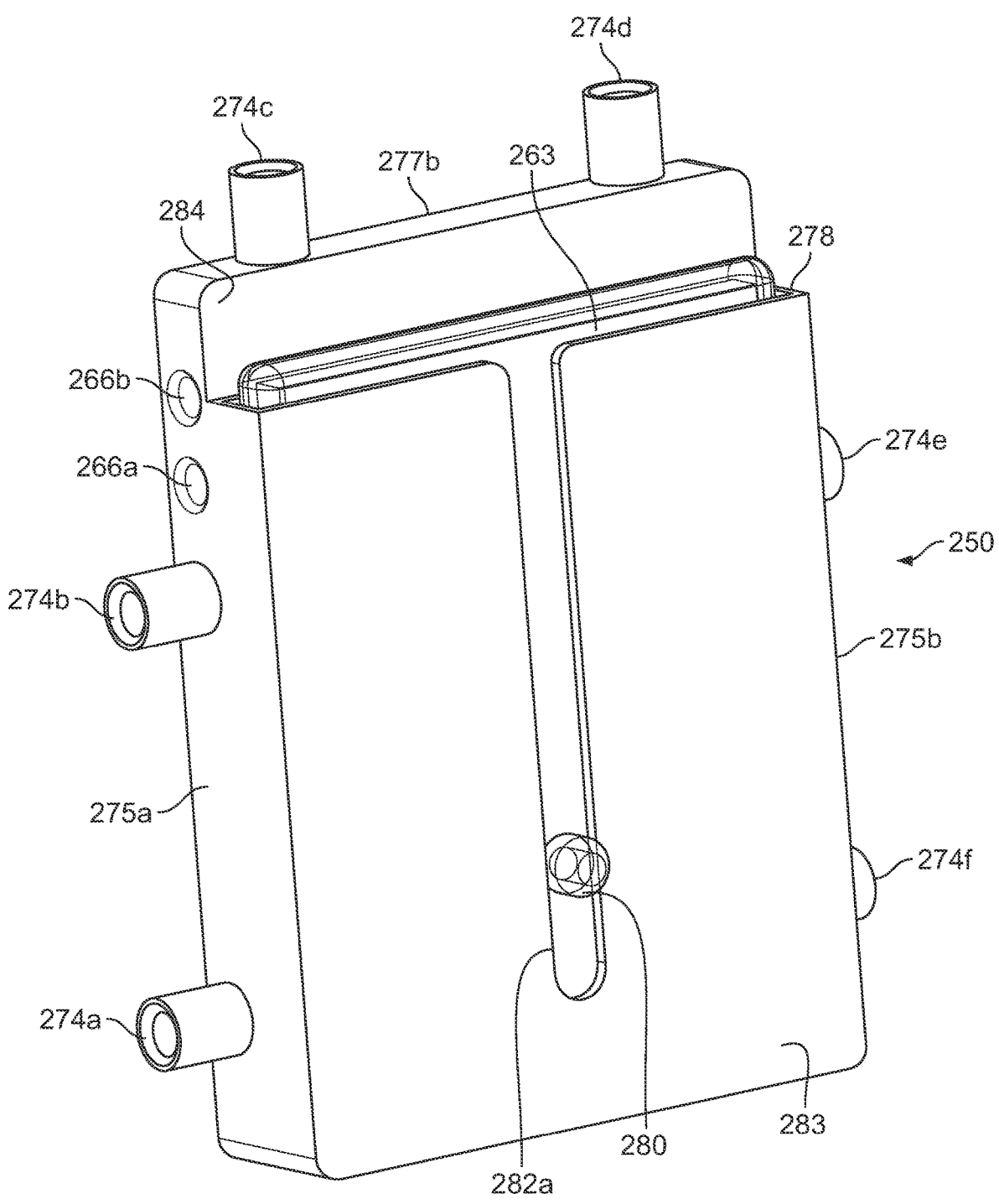
FIG. 9 is a perspective view of a second fluid processing cassette according to an aspect of the present disclosure.
Figure 10:
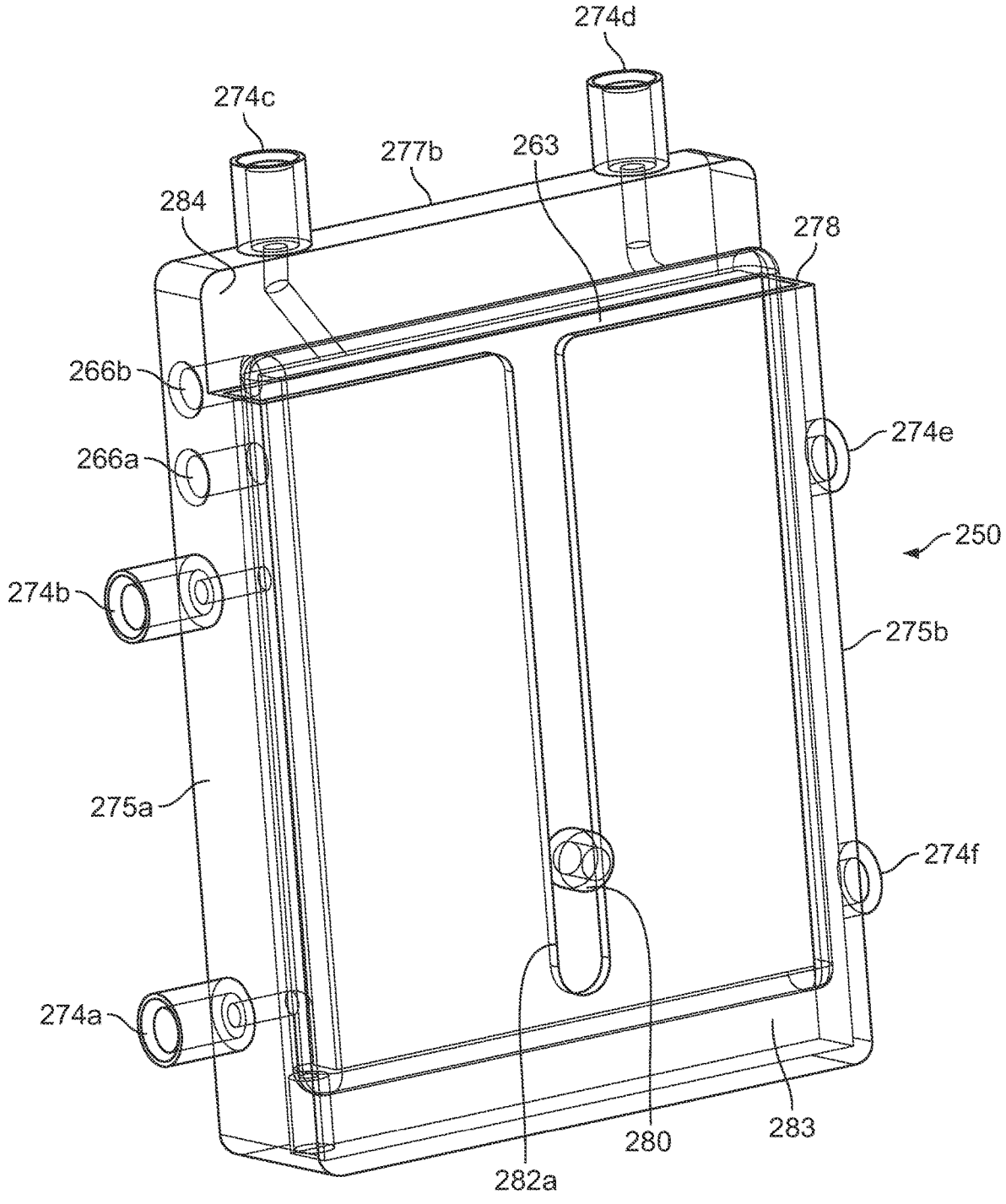
FIG. 10 is a perspective transparent view of the second fluid processing cassette of FIG. 9.
Figure 11:
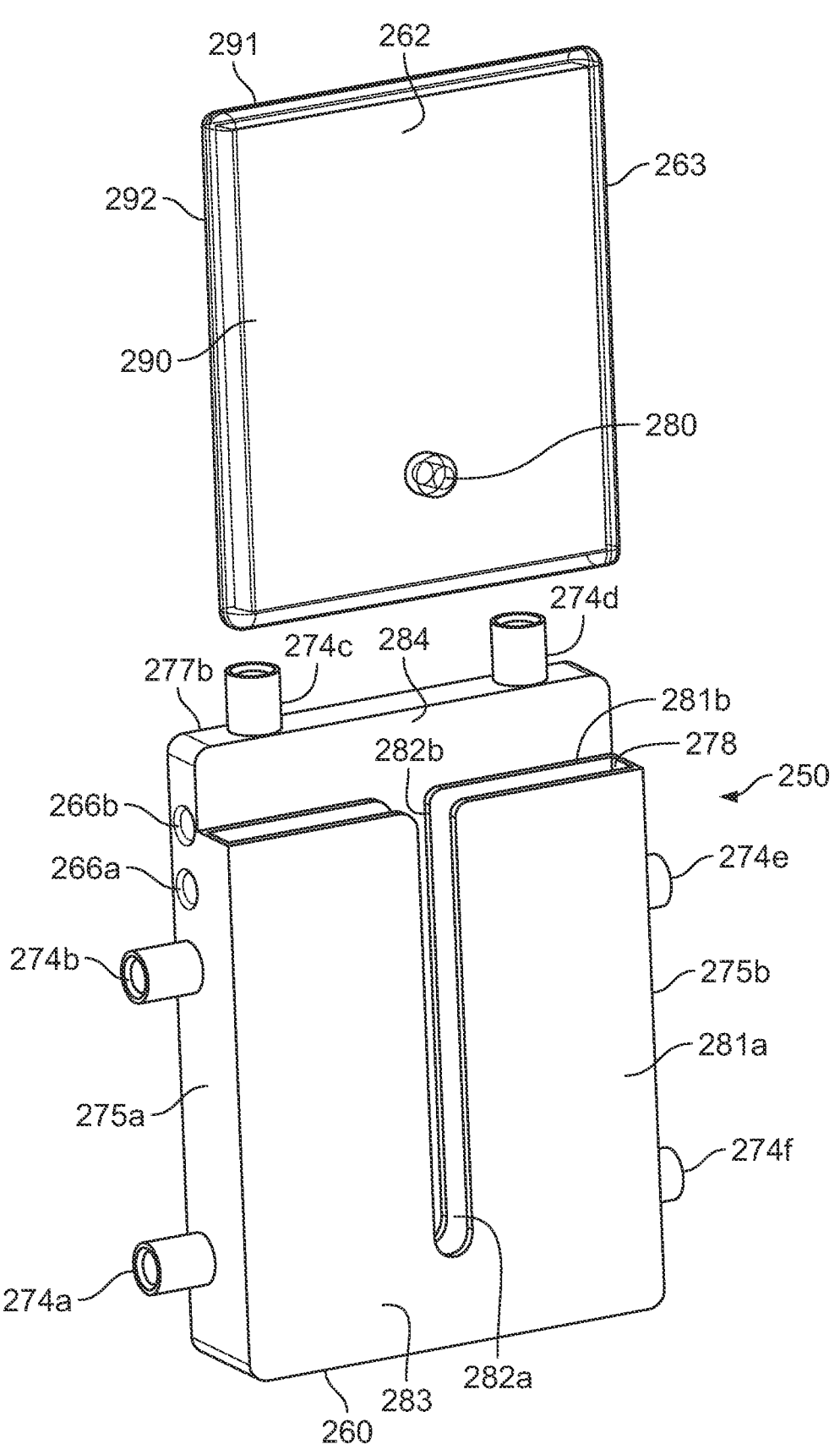
FIG. 11 is a perspective exploded view of the second fluid processing cassette of FIG. 9.
Figure 12:
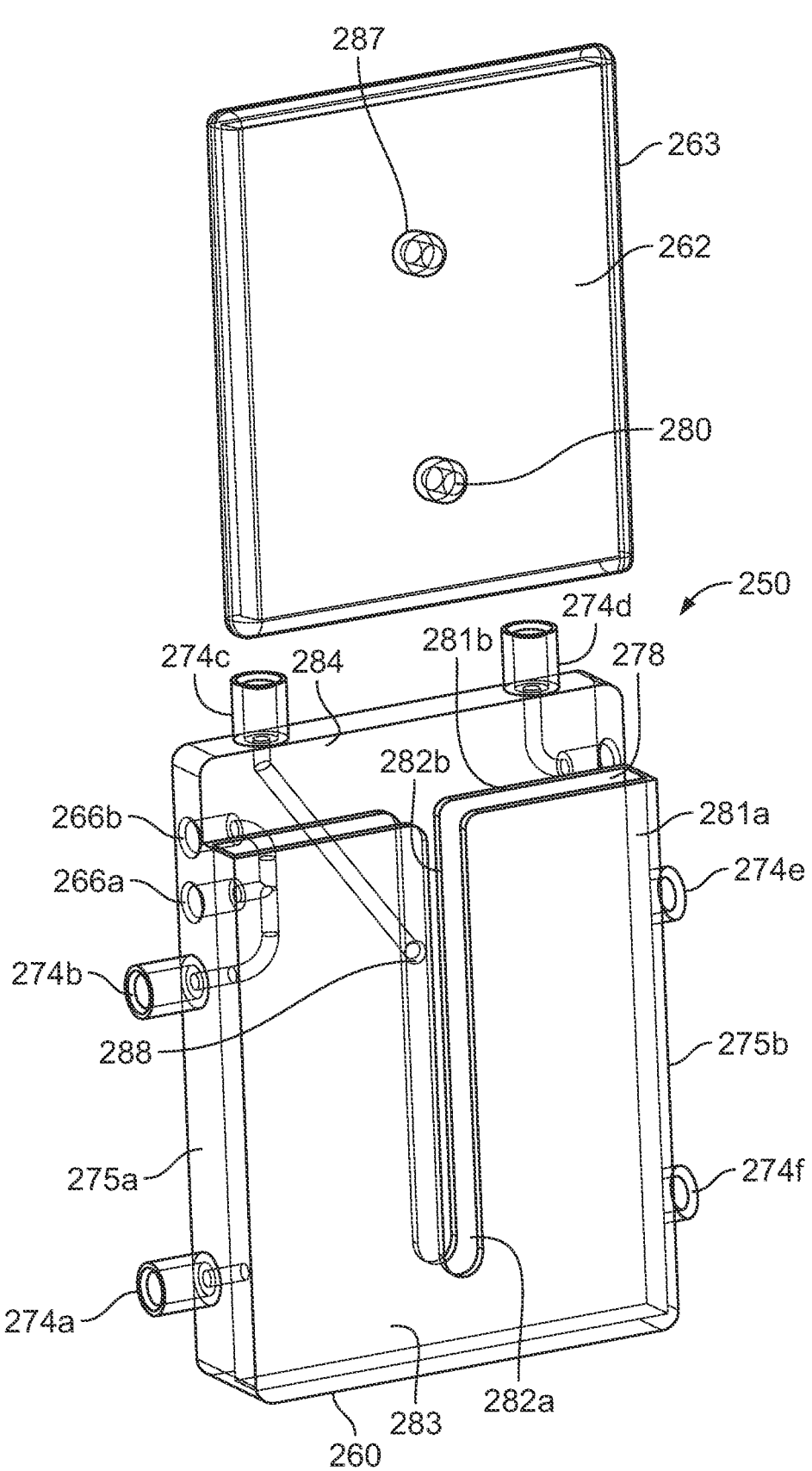
FIG. 12 is a transparent perspective exploded view of the second fluid processing cassette of FIG. 9.

The perimeter of the illustrated cassette body 160 also includes tubing ports 174a, 174b, 174c, 174d, 174e, and 174f, with FIG. 8 showing a first tubing loop 165a connected to the cassette at ports 174a and 174b, a second tubing loop 165b connected to the cassette at ports 174c and 174d, and a third tubing loop 165c connected to the cassette at ports 174e and 174f. Although three tubing loops are shown (for association with pumps 16, 18, and 20), more or fewer may be utilized depending on the number of associated pumps. Additionally, as noted above, differently configured pump mechanisms may be incorporated into the cassette 150 (e.g., pump chambers associated with a flexible diaphragm configured to be actuated by reciprocating pump heads) without departing from the scope of the present disclosure.

In addition to the ports positioned along the perimeter of the cassette body 160, the cassette body 160 additionally includes a filter inlet port 170 defined in the first wall or face 185. As will be described in greater detail, the filter inlet port 170 is configured to allow for fluid (or a fluid component) to exit the cassette body 160 and flow into a filter or filtration medium 162 positioned between the first wall or face 185 and the cap 164 (FIGS. 5-7). Although filter inlet port 170 is shown as being located toward the bottom side or edge 177a of the cassette body 160, it may be incorporated into any suitable portion of the first wall or face 185.

As for the cap 164, the illustrated embodiment includes a filter outlet port 168. As will be described in greater detail, the outlet port 168 is configured to direct filtered fluid (or a filtered fluid component) out of the cassette 150, so the outlet port 168 may be configured to be placed into fluid communication with an appropriate destination (e.g., with the port 168 be connected to a red blood cell collection container 46 via a tube or conduit when the filter is configured to filter packed red blood cells).

Figure 4:
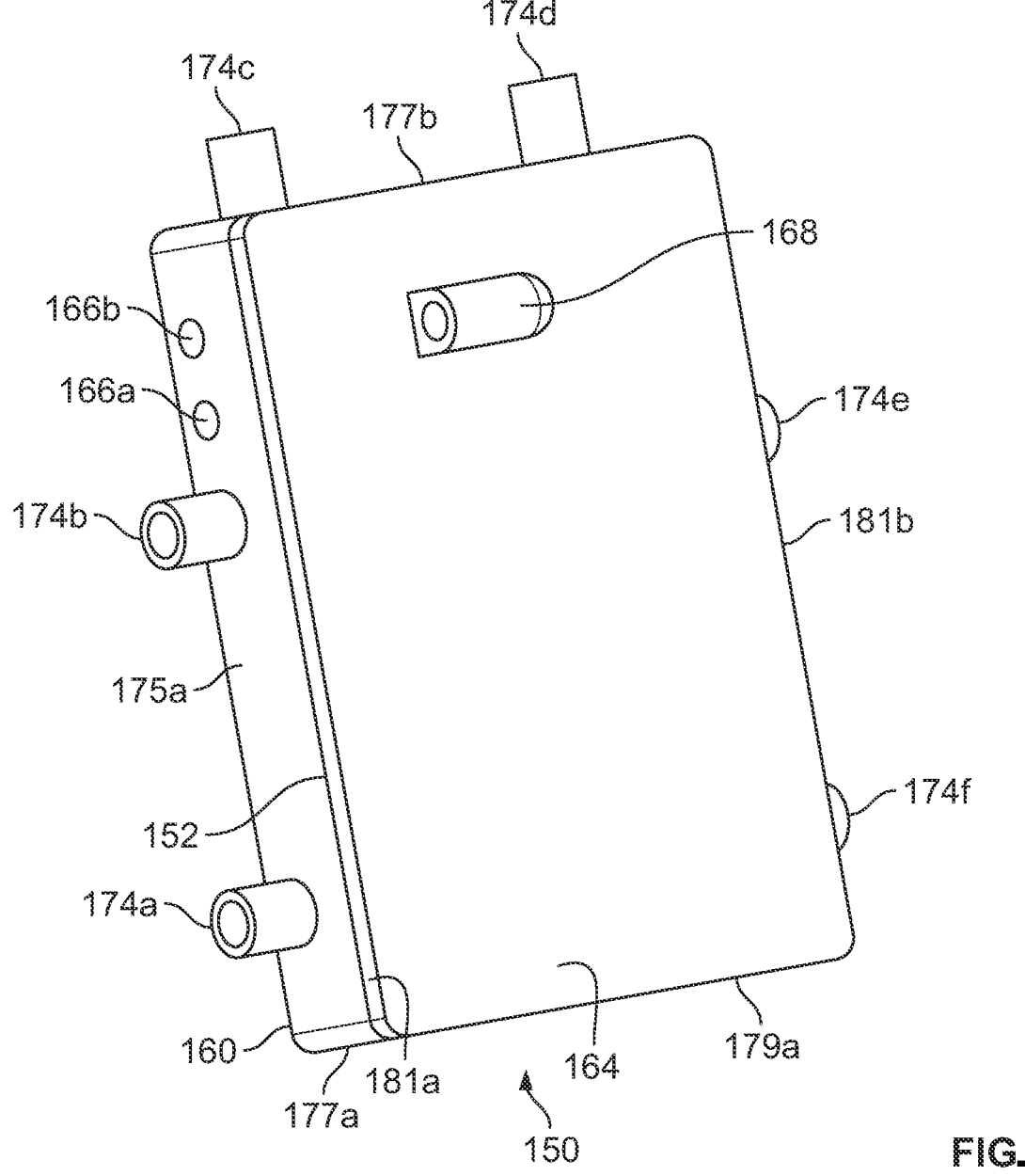
FIG. 4 is a perspective view of a first fluid processing cassette according to an aspect of the present disclosure.

As noted above, the body and cap components 160 and 164 are configured to be secured together to define the cassette 150. The body 160 and cap 164 may be joined by any suitable approach, provided that a fluid-tight seal is formed therebetween. In the embodiment shown in FIGS. 4-8, the cap and body are joined along their perimeters at a join or seal line 152 (FIG. 4). According to one exemplary approach, the seal between the body 160 and cap 164 are formed by the application of pressure and radio-frequency heating to the cap and body. In another exemplary approach, the body and cap are welded together by a suitable plastic welding process, such as hot plate welding or ultrasonic welding.

The illustrated cap 164 includes a projection 173 and the body 160 defines a recess 171 configured to receive the projection 173 to define a cavity, with the filter inlet port 170 and the filter outlet port 168 opening into the cavity. A filter or filtration medium 162 is received within the cavity, positioned between the projection 173 and the recess 171, as shown in FIG. 5-7. Preferably, the filtration medium 162 is fully positioned within the between the cap and body when the cassette 150 is fully assembled, though it is within the scope of the present disclosure for a portion of the filtration medium 162 to extend outside of the cavity.

The filtration medium 162 may be variously configured, depending on the nature of the substance(s) to be removed or separated from the biological fluid or fluid component passed through the filtration medium 162. For example, the filtration medium 162 may be configured to remove a substance or substances from a biological fluid or fluid component by depth filtration or by a binding material that retains the targeted substance(s) while allowing the other components of the biological fluid or fluid component to flow through the filtration medium 162. In an exemplary embodiment, the filtration medium 162 is configured to separate leukocytes from blood or a blood component (e.g., packed red blood cells) or some other leukocyte-containing fluid by depth filtration, in which case the filtration medium 162 may be formed of a fibrous or non-fibrous material having pores sized to trap leukocytes within the filtration medium 162, while allowing other components of the biological fluid or fluid component to pass through. The filtration medium 162 may be formed of any suitable material but, in one exemplary embodiment, is formed of a melt-blown, nonwoven, fibrous material, such as a polybutylene terephthalate ("PBT") material.

In one embodiment, the filtration medium 162 is formed from a plurality of layers, which may be either substantially identical or differently configured. For example, a multi-layer filtration medium may be comprised of a plurality of fibrous layers, a plurality of non-fibrous layers, or a combination of fibrous layers and non-fibrous layers. While a multi-layer filtration medium may be preferred for improved filtration performance, it is also within the scope of the present disclosure for the filtration medium to be a single-layer component.

Regardless of the particular configuration of the filtration medium 162, it will be seen that, by incorporating it into the cassette 150, the processing device 10 does not require a dedicated or specialized receptacle for a filter. This allows for a decreased device footprint and complexity of installation when mounting the fluid flow circuit 12 to the processing device 10.

In addition to the filtration medium 162, the fluid processing cassette may include additional components positioned within the cavity between the body and the cap of the cassette. This may include, for example, a pre-filter at least partially positioned between the body 160 and the filtration medium 162 and/or a post-filter at least partially positioned between the filtration medium 162 and the cap 164. If provided, it may be advantageous for each of the pre-filter and post-filter to be fully positioned within the cavity, with the filtration medium 162 being sufficiently sized and configured to prevent a fluid or fluid component flowing into the cavity from reaching the filter outlet port 168 without passing first through the pre-filter and then through the filtration medium 162 and then through the post-filter.

The pre-filter and/or post-filter may be variously configured, though it may be advantageous for each to be configured as a planar or sheet-like component with a shape that is congruent to the filtration medium 162. For example, in the illustrated embodiment, the pre-filter and/or post-filter may have a generally rectangular configuration, which matches the generally rectangular configuration of the associated filtration medium 162 and cavity. In such an embodiment, the pre-filter and/or post-filter may be secured to the filtration medium 162 at or adjacent to their perimeters or may be separately provided. While it may be preferred for the perimeter of the pre-filter and/or post-filter to be substantially the same size and shape as the filtration medium 162, it is also within the scope of the present disclosure for the perimeter of the pre-filter and/or post-filter to be differently sized and shaped from the perimeter of the associated filtration medium 162.

The pre-filter, if provided, may be configured to allow the passage of a biological fluid or fluid component to be filtered therethrough. Preferably, the pre-filter has different filtration properties (e.g., porosity) than the associated filtration medium 162. In one embodiment, the pre-filter has larger pores than the associated filtration medium 162. If the filtration medium is provided as a leukofilter, the pre-filter may be configured to remove microaggregates from the biological fluid or fluid component prior to the fluid or fluid component encountering the filtration medium 162. In such an application, it may be advantageous for the pre-filter to be comprised of a polyethylene terephthalate ("PET") material. In other applications, other material compositions may be employed. The pre-filter may be provided as a single-sheet or single-piece component or as a multi-sheet or multi-piece, stacked component.

As for the post-filter, if provided, it may be configured as a single-sheet or single-piece component or as a multi-sheet or multi-piece, stacked component. The post-filter may be configured to be especially porous, allowing for a filtered fluid or fluid component to flow freely therethrough. For example, the post-filter may be configured as a mesh or lattice having relatively large pores or openings and formed of a polyvinyl chloride ("PVC") material or the like. In such an embodiment, the post-filter provides a manifold effect and prevents the filtration medium 162 from engaging the cassette cap 164, thereby allowing for the filtered fluid or fluid component to freely flow to the filter outlet port 168 without becoming entrapped within the filtration medium 162.

In addition to (or instead of) a manifold effect being provided by a pre-filter and/or a post-filter, the body and/or cap of the cassette may include a plurality of protrusions 172 (on the cassette body) and 176 (on the cassette cap) that project into the cavity, toward the filter 162. The protrusions may be composed of the same material as that of the body and cap of the cassette 150 (in which case they may be molded or otherwise integrally formed with the body or cap) or may be separately provided and secured to the cassette. The protrusions may be variously configured (e.g., as cylinders or truncated cones or truncated pyramids) without departing from the scope of the present disclosure, which may include all of the protrusions being similarly or identically configured or two or more of the protrusions being differently configured. In an exemplary embodiment, the protrusions protrude in range of about 0.025 inch to about 0.0625 inch. The protrusions function to enhance the flow adjacent to the filtration medium 162 by providing space between the opposing faces of the cavity and the filtration medium 162, thereby keeping the flow path open. With this in mind, the protrusions may be arranged in any desirable manner on the cap and/or case so as to improve fluid flow. For example, FIG. 6 depicts protrusions in a plurality of horizontal rows, but alternative arrangements of the protrusions are possible. In embodiments in which both the cassette body and the cap are provided with protrusions, it may be advantageous for the protrusions of the body to be misaligned with the protrusions of the cap in order to prevent the protrusions from pressing against each other and compressing the filtration medium 162 therebetween, which could hinder fluid flow. Additionally, in order to improve fluid flow, characteristics of the protrusions such as the amount of protrusions, length, size, shape, and pattern may be selected based on the type of fluid to be filtered.

While FIGS. 4-8 illustrate an embodiment in which a filter is incorporated into a cassette 150, FIGS. 9-13 illustrate an embodiment in which a filter is received within an external slot of a biological fluid processing cassette 250. Components in common between the first and second embodiments are numbered similarly (e.g., with corresponding ports of the two embodiments being identified as 174*a-f* in the first embodiment and as 274*a-f* in the second embodiment) and may be provided in accordance with the foregoing description of the corresponding component.

Figure 13:
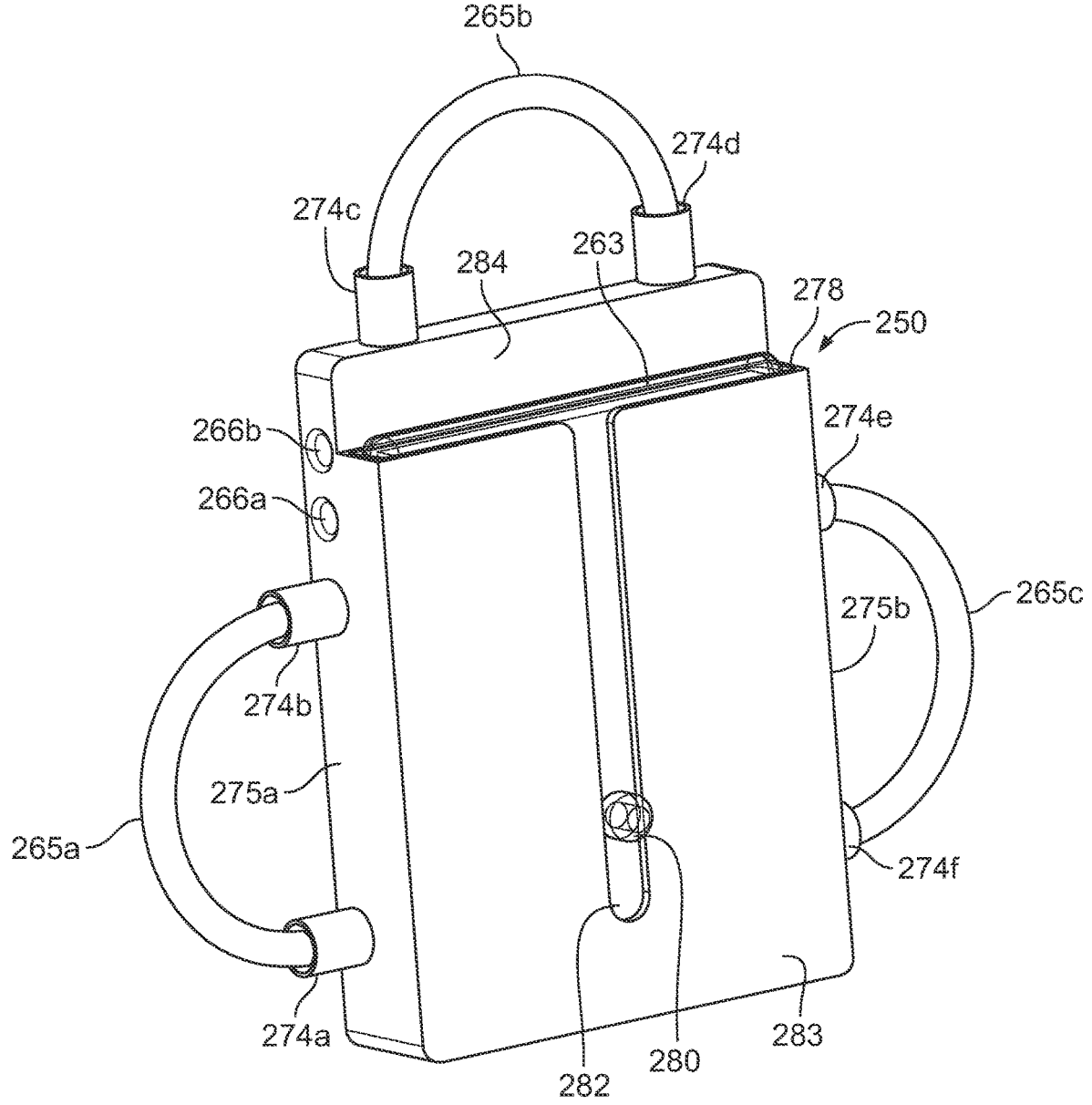
FIG. 13 is a perspective view of the second fluid processing cassette of FIG. 9 with pump tubing included.

The cassette 250 includes a cassette body 283 that may be similarly configured to the cassette body of the first embodiment, with side edges or walls 275*a* and 275*b* and bottom and top edges or walls 277*a* and 277*b*, defining a plurality of internal fluid flow paths and including various ports. FIG. 13 shows the second fluid processing cassette with tubing attached, arranged similarly to the tubing of the first fluid processing cassette of FIG. 8. The tubing 265*a*, 265*b*, 265*c*, may be in contact with pumps 16, 18, 20, which may serve to push the fluid through the cassette 250. The first tubing 265*a* may be connected to the cassette at ports 274*a* and 274*b*, second tubing 265*b* may be connected to the cassette at ports 274*c* and 274*d*, and third tubing 265*c* may be connected to the cassette at ports 274*e* and 274*f*. Although three tubing sets are shown, more or fewer may be utilized depending on the number of associated pumps, with differently configured pump mechanisms also being possible, as described above with regard to the embodiment of FIGS. 4-8.

One notable difference between the cassette bodies of the two illustrated embodiments is that the cassette body 283 of FIGS. 9-13 is not configured to be secured to a cap to enclose a filter within an internal cavity, but rather has a slot 278 projecting from its front face 284. Although the slot is shown on the front face 284, it may also be on back face of the cassette body.

The slot is configured to receive all or at least a portion of an associated filter 263, which may be variously configured without departing from the scope of the present disclosure. In the illustrated embodiment, the filter 263 is generally rectangular, with a filtration medium 262 enclosed within a soft or flexible housing or shell, and with walls of the slot providing support for the filter 263. By way of example, a soft-shelled filter may be provided as a Fresenius Kabi Bioflex RBC leukofilter, or any other soft-shelled filter described in the art, such as the soft-shelled filter of US Patent Publication Number 10,376,627, which is hereby incorporated herein by reference.

If provided as a soft-shelled filter, the walls 290 and 292 of the filter housing may be separate sheets of flexible material which may be formed of a PVC material or any other suitable material (preferably a flexible, medical grade plastic material) through which the biological fluid will not flow. In another embodiment, the first and second walls 290 and 292 of the filter housing may be opposing faces of a generally tubular piece of material or two portions of a single sheet of material that is folded onto itself.

Such a filter 262 includes a seal 291, which joins the two walls 290 and 292 of the filter housing to prevent leakage, with the seal optionally also including a perimeter of the filtration medium. The seal 291 may be formed by any suitable sealing process, such as the application of pressure and radio-frequency heating to the two walls 290 and 292 of the filter housing and the interior components of the filtration medium positioned therebetween. Preferably, the seal

291 forms a complete seal at or adjacent to the perimeters of the interior components of the filter to prevent the biological fluid from "shortcutting" the interior components from an inlet of the filter to an outlet without passing through all of the interior components of the filter 262.

As with the filtration medium 162 of the first embodiment, filtration medium 262 may be variously configured, depending on the nature of the substance(s) to be removed or separated from the biological fluid passed through the filtration medium 262, with the above discussion relating to the filtration medium 162 being also applicable to the filtration medium 262. As also described above, the filter 263 may include additional components positioned between the walls 290 and 292 of the filter, such as a pre-filter and/or a post-filter. The filter may include rigid walls, rather than a flexible housing, although a flexible filter may be preferred for various reasons.

As the filter 263 may be variously configured without departing from the scope of the present disclosure, it should be understood that the configuration of the slot may also vary (in order to conform to the configuration of the associated filter) without departing from the scope of the present disclosure. For example, in the illustrated embodiment, the filter 263 is generally rectangular, in which case the slot may be generally rectangular and of a suitable size to accommodate all or a portion of the filter 263.

The illustrated slot 278 includes a first and second wall 281*a* and 281*b*, Each wall of the slot may include an elongate opening or channel 282*a*, 282*b* configured to accommodate a portion of the filter 263 projecting from the filter 263 as the filter 263 is advanced into the slot 278 via an open end of the slot. In the illustrated embodiment, the elongate openings are similarly sized and configured, but it is within the scope of the present disclosure for the elongate openings to be differently sized and/or shaped. It is also within the scope of the present disclosure for only one of the walls of the slot to include an associated opening or channel or for neither to include an opening or channel. However, in an exemplary embodiment (which may be suitable for use with a conventionally configured filter having a soft or flexible housing), the elongate opening 282*a* of the first wall 281*a* is configured to accommodate a first port 280 projecting from a surface of the filter, while the elongate opening 282*b* of the second wall 281*b* is configured to accommodate a second port 287 (FIG. 12) projecting from an opposing surface of the filter. Typically, the ports of the filter are relatively rigid compared to the filter housing (e.g., with the ports comprising molded components formed of a plastic material or the like), which is why the elongate openings may be advantageous to accommodate such ports.

The cassette body 283 may include a cassette port 288 (FIG. 12) on face 284 for connecting one of the flow paths to one of the ports of the filter. The cassette port 288 may be in communication with the associated port of the filter by any suitable means, such as flexible tubing. It should be understood that this is not the only port of the cassette that may be fluidically connected to the filter, as any other port (e.g., port 266*a*) of the cassette may instead be fluidically connected to the filter. As with the first fluid processing cassette, whichever port of the filter that is not fluidically connected to the cassette port 288 may be in fluid communication with the appropriate destination (e.g., a filtered fluid component container). It is also within the scope of the present disclosure for a fluid or fluid component to enter the filter from the cassette via one of the filter ports and then be conveyed back into the cassette (via a different cassette port), rather than being directly conveyed from the filter to a separate container or the like.

As either filter port may be placed into fluid communication with a cassette port, it should be clear that either filter port may serve as an inlet port, with the other filter port serving as an outlet port. Thus, in one embodiment, an unfiltered fluid or fluid component may be conveyed into the filter via port 280, with the filtered fluid or fluid component exiting the filter via port 287. In an alternative embodiment, an unfiltered fluid or fluid component may instead be conveyed into the filter via port 287, with the filtered fluid or fluid component exiting the filter via port 280.

In addition to the elongated openings, the slot may be otherwise configured as necessary to accommodate an associated filter when the filter is advanced into the slot. This may include a latch or the like configured to retain the filter in place within the slot and/or one or more protrusions of the type described above with regard to the embodiment of FIGS. 4-8 to provide a manifold effect (though such a manifold effect may be less advantageous in the embodiment of FIGS. 9-13, as the filter may be configured to not require such external support).

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

Aspects

Aspect 1. A biological fluid processing cassette comprising a rigid cassette body defining at least a portion of a cavity and a filter inlet port opening into the cavity; a rigid cap secured to the cassette body to seal the cavity and defining a filter outlet port opening into the cavity; and a filtration medium sealed within the cavity for filtration of a biological fluid flowing through the cavity from the filter inlet port to the filter outlet port.

Aspect 2. The cassette of Aspect 1, wherein the filtration medium is configured to remove leukocytes from whole blood.

Aspect 3. The cassette of Aspect 1, wherein the filtration medium is configured to remove leukocytes from a separated blood component.

Aspect 4. The cassette of any one of the preceding Aspects, wherein the cassette body defines a plurality of protrusions extending into the cavity.

Aspect 5. The cassette of Aspect 4, wherein all of said protrusions are similarly configured.

Aspect 6. The cassette of any one of the preceding Aspects, wherein the cap defines a plurality of protrusions extending into the cavity.

Aspect 7. The cassette of Aspect 6, wherein all of said protrusions are similarly configured.

Aspect 8. The cassette of any of the preceding Aspects, wherein both the cassette body and the cap define a plurality of protrusions extending into the cavity.

Aspect 9. The cassette of Aspect 8, wherein all of said protrusions are similarly configured.

Aspect 10. The cassette of any one of Aspects 8-9, wherein the protrusions of the cassette body are misaligned with the protrusions of the cap.

Aspect 11. The cassette of any one of the preceding Aspects, wherein the cassette body and cap each have a first and second side wall and a top and bottom wall, the cassette body defines a recess from each of the side walls and the top and bottom walls, the cap includes a projection from each of the side walls and the top and bottom walls and the recess is sized to receive the projection so as to define at least a portion of the cavity.

Aspect 12. The cassette of Aspect 11, wherein the filtration medium is secured between the recess and the projection.

Aspect 13. A biological fluid processing cassette comprising a rigid cassette body defining a plurality of internal fluid flow paths, an external slot, and a cassette port allowing fluid communication between at least one of said fluid flow paths and the slot; and a filter configured to be received within the slot of the cassette body and including an inlet port and an outlet port, wherein one of the inlet port and the outlet port is configured to be placed into fluid communication with the cassette port when the filter is received within the slot.

Aspect 14. The cassette of Aspect 13, wherein the filter is configured to remove leukocytes from whole blood.

Aspect 15. The cassette of Aspect 13, wherein the filter is configured to remove leukocytes from a separated blood component.

Aspect 16. The cassette of Aspect 13, wherein the slot is associated with a front face of the cassette body, the cassette port is incorporated into the front face of the cassette body, and the filter is configured to be received within the slot with the inlet port of the filter positioned adjacent to the front face of the cassette body and the cassette port in fluid communication with the inlet port of the filter.

Aspect 17. The cassette of Aspect 13, wherein the slot is associated with a front face of the cassette body, the cassette port is incorporated into the front face of the cassette body, and the filter is configured to be received within the slot with the outlet port of the filter positioned adjacent to the front face of the cassette body and the cassette port in fluid communication with the outlet port of the filter.

Aspect 18. The cassette of any one of Aspects 13-17, wherein the slot includes an elongate opening configured to accommodate the inlet port of the filter when the filter is advanced into the slot.

Aspect 19. The cassette of any one of Aspects 13-18, wherein the slot includes an elongate opening configured to accommodate the outlet port of the filter when the filter is advanced into the slot.

Aspect 20. The cassette of Aspect 13, wherein the slot includes first and second elongate openings, the first elongate opening is configured to accommodate the inlet port of the filter when the filter is advanced into the slot, and the second elongate opening is configured to accommodate the outlet port of the filter when the filter is advanced into the slot.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A biological fluid processing cassette comprising:
a rigid cassette body comprising a first face and a second face defining therebetween a plurality of fluid flow paths each extending through the cassette body, with the cassette body defining a first cavity in which said plurality of fluid flow paths are defined, at least a portion of a second cavity, and a filter inlet port opening into the second cavity, wherein at least one of the fluid flow paths does not open into the second cavity;
a rigid cap secured to the cassette body to seal the second cavity and defining a filter outlet port opening into the second cavity, wherein the first face is positioned opposite of the cap, with the filter inlet port incorporated into the first face; and
a filtration medium sealed within the second cavity between the cap and the first face for filtration of a biological fluid flowing through the second cavity from the filter inlet port to the filter outlet port, wherein the cap and/or the first face defines a plurality of protrusions extending into the second cavity.

2. The cassette of claim 1, wherein the filtration medium is configured to remove leukocytes from whole blood.

3. The cassette of claim 1, wherein the filtration medium is configured to remove leukocytes from a separated blood component.

4. The cassette of claim 1, wherein the first face defines at least two of said plurality of protrusions extending into the second cavity.

5. The cassette of claim 4, wherein all of said protrusions defined by the first face are similarly configured.

6. The cassette of claim 1, wherein the cap defines at least two of said plurality of protrusions extending into the second cavity.

7. The cassette of claim 6, wherein all of said protrusions defined by the cap are similarly configured.

8. The cassette of claim 1, wherein each of the first face and the cap defines at least two of said plurality of protrusions extending into the second cavity.

9. The cassette of claim 8, wherein all of said protrusions are similarly configured.

10. The cassette of claim 8, wherein the protrusions of the first face are misaligned with the protrusions of the cap.

11. The cassette of claim 1, wherein
the cassette body and cap each have a first side and a second side and a top side and bottom side,
the cassette body defines a recess spaced inwardly from each of said sides of the cassette body,
the cap includes a projection spaced inwardly from each of said sides of the cap, and the recess is sized to receive the projection so as to define at least a portion of the second cavity.

12. The cassette of claim 11, wherein the filtration medium is secured between the recess and the projection.

13. The cassette of claim 1, wherein the cassette body further includes a plurality of ports along a perimeter of the cassette body.

14. The cassette of claim 1, wherein the cassette body further comprises a top side and a bottom side and the filter inlet port is located closer to the bottom side of the cassette body than to the top side of the cassette body.

15. The cassette of claim 1, wherein the filtration medium is fully positioned between the first face and the cap.

16. The cassette of claim 1, wherein the filtration medium includes a plurality of layers.

17. The cassette of claim 1, further comprising a pre-filter fully positioned within the second cavity.

18. The cassette of claim 1, further comprising a post-filter fully positioned within the second cavity.

19. The cassette of claim 1, wherein a fluid-tight seal is formed between the cassette body and the cap.

20. The cassette of claim 1, wherein the cap is configured to define a perimeter that matches a perimeter of the cassette body, such that a perimeter of the cassette has a generally smooth or continuous perimeter.

21. A biological fluid processing cassette comprising:
a rigid cassette body comprising a first face and a second face defining therebetween a plurality of fluid flow paths each extending through the cassette body, with the cassette body defining at least a portion of a cavity and a filter inlet port opening into the cavity, wherein at least one of the fluid flow paths does not open into the cavity;
a rigid cap secured to the cassette body to seal the cavity and defining a filter outlet port opening into the cavity, wherein the first face is positioned opposite of the cap, with the filter inlet port incorporated into the first face; and
a filtration medium sealed within the cavity between the cap and the first face for filtration of a biological fluid flowing through the cavity from the filter inlet port to the filter outlet port, wherein the cap and/or the first face defines a plurality of protrusions extending into the cavity, wherein
the cassette body includes a plurality of edges extending from the first face to the second face,
a plurality of ports are incorporated into said plurality of edges of the cassette body, and
each port is fluidically connected to at least one of said fluid flow paths.

* * * * *